United States Patent [19]

Hoffmann

[11] Patent Number: 4,994,391
[45] Date of Patent: Feb. 19, 1991

[54] BACTERIA CULTURING SYSTEM

[76] Inventor: Craig O. Hoffmann, 10364 Newport Dr., Eden Prairie, Minn. 55347

[21] Appl. No.: 372,674

[22] Filed: Jun. 28, 1989

[51] Int. Cl.$^5$ ............................................. C12M 3/02
[52] U.S. Cl. .................................... 435/286; 435/313; 435/316; 210/601; 210/605
[58] Field of Search ............... 435/286, 304, 309, 313, 435/314, 316, 290; 47/1.4, 59, 60; 210/601, 605, 205, 220.2

[56] References Cited

U.S. PATENT DOCUMENTS

| | | | |
|---|---|---|---|
| 3,546,812 | 12/1970 | Kobayashi et al. | 210/605 X |
| 4,008,159 | 2/1977 | Besik | 210/601 |
| 4,264,740 | 4/1981 | Christ et al. | 435/316 X |
| 4,522,722 | 6/1985 | Nicholas | 210/605 |
| 4,724,214 | 2/1988 | Mori | 435/313 X |
| 4,812,237 | 3/1989 | Cawley et al. | 210/605 |
| 4,824,563 | 4/1989 | Iwahori et al. | 210/605 X |
| 4,857,458 | 8/1989 | Nobilet et al. | 435/316 |

Primary Examiner—Larry Jones
Attorney, Agent, or Firm—Lawrence M. Nawrocki

[57] ABSTRACT

An improved bacterial culturing system which is advantageously used "on-site" at waste water treatment plants. The system rapidly and efficiently produces various types of bacteria having enhanced activity and controllable characteristics. The bacteria are used to break down undesired or unwanted chemical species contained in the waste water stream. The system includes a unique culturing or primary basin in communication with an acclimation or acclimator basin. Bacteria grown in the culturing basin are partially exposed to the materials they are later intended to break down in the acclimation basin.

21 Claims, 6 Drawing Sheets

BACTERIA CULTURING SYSTEM

TECHNICAL FIELD

This invention is in the field of bacteria culturing. More particularly, this invention is in the field of systems for culturing aerobic and anaerobic bacteria. Yet more particularly, this invention is in the field of "on-site" bacterial culturing systems used to generate highly active bacteria for the breakdown of chemical or biological unwanted solids suspended or partially dissolved in aqueous media such as, for example, waste water effluents.

BACKGROUND OF THE INVENTION

There exists a strong environmental and economic demand for accelerated activity bacteria capable of breaking down unwanted solids suspended or partially dissolved in aqueous media. Such solids have been classified in several ways including: total suspended solids (TSS), total volatile solids (TVS), sludge, and collectively, fats, oils and greases (FOG). Such solids have also been classified in their ability to enhance the life-bearing capabilities of the liquid in which they are suspended. Normal classifications include chemical oxygen demand (COD) and biological oxygen demand (BOD). Accelerated activity bacteria (i.e. highly active bacteria) have also been used to breakdown certain toxic wastes such as phenolic compounds and chromium by-products.

In a typical application, active bacteria, after acclimation, are used to treat toxic wastes to produce harmless, easily disposed non-toxic end products. Highly active bacteria have also been used to control or eliminate malodorous aqueous effluents. Malodorous substances such as hydrogen sulfide, ammonia or butyric acid, if broken down or denatured, are essentially odorless. An example of a material which falls in both the classifications of toxic material and malodorous material is hydrogen sulfide which, in its gaseous form or an aqueous solution is both toxic and malodorous.

Several strains of bacteria, normally found in soil, have been found to significantly shorten the breakdown cycle of solid wastes generally found in sewage. Examples of such soil bacteria include the genera of Arthrobacter, Bacillus, Pseudomonas, Flavobacterium and Acinetobacter, to mention a few. Certain bacteria found in animal intestines have been found to produce enzymes which, in turn, preferrably breakdown fats, oils and greases. Examples of such enzymes are found in many ruminant animals. Especially of note are the lipase producers found in sheep. Lastly, bacteria including varieties of Rhodospirillum and Chromatium are commonly found in salt water and have been found to rapidly and efficiently breakdown aqueous solutions of hydrogen sulfide. These are but a few examples of the many circumstances in which bacteria found in one environment can be usefully employed to remove unwanted species and solutes in other environments.

The problem of identifying bacteria from one environment useful to remove an unwanted species from another environment has been exacerbated by difficulties in isolating the bacteria, culturing them, transporting them to the new site for application and maintaining their activity while stored on-site. The use of water as a transporting agent (from manufacturer to plant) has the problem of limited bacterial counts and short shelf life of the bacteria. Two other techniques presently used for preserving the activity of bacteria include mixing the bacteria with bran media and freeze-drying (lyophilizing). Mixing bacteria with bran has the unfortunate drawback of dramatically increasing the time between dispensing the bran/bacterial medium into the effluent stream to be treated and full activity of the bacteria. In instances where bacteria need to be acclimated, e.g., where toxic wastes are to be treated, further time for acclimation is required. Futhermore, the bran itself creates sludge.

Freeze-drying of bacterial product to enhance its shelf life has the unfortunate drawbacks of the increased cost associated therewith. Also, freeze-dried bacteria need to be rehydrated prior to achieving optimal activity.

The net effect of these problems and issues is that even with the substantial ecological advantage of the use of bacterial cultures to treat unwanted materials in, for example, waste water, economic considerations have limited their utilization. This is not to say that no efforts have been made to culture specific bacterial products on-site at waste water treatment plants. The systems used in these "on-site" applications have typically been easily disturbed and were capable of producing only limited amounts of the desired bacteria for the space required.

Such systems only provide food and light (when necessary), and they are under the control of the bacterial manufacturer. The intent is to allow the purchaser the ability to culture its own specialized strains of bacteria, blended and acclimated especially for the given environment. The systems are designed for use on solids and liquids including applications such as toxic waste sites, industrial plants, and air scrubber systems as a replacement to chemicals such as potassium permanganite and sodium hydroxide.

Surface area may be provided within a plant, but not for the purpose of selective bacterial culturing. These systems are designed to allow the waste to come in contact with the flow of solids. The systems include a trickling filter and rotating biological disks. They are not attempting to culture high quality bacteria, but are capturing whatever bacteria exists within a given flow. These bacteria are subject to upsets due to changes in the liquid, including pH variations, temperature changes and chemicals present. Upsets take from four to ten days, sometimes longer, to recover without the addition of a highly concentrated bacterial solution. With this solution, recovery can be as rapid as four hours, and will typically be complete within twelve hours.

The system-cultured bacteria are within a given basin that uses a highly controlled environment to optimize the growth of a given culture on the existing location, to optimize the treatment of sewage, to reduce or concentrate hazardous waste, to act within an air scrubber to break down the collected chemicals within the system, to break down fats, oils, and greases, and to reduce the volume of sludge in waste water.

It is known that various bacterial systems containing separate species of bacteria tend to symbiotically reduce complex masses of unwanted materials to harmless gases, water, and simple harmless substances. Such symbiotic bacterial reductions are more successful if large reproductive surface areas are provided.

This "on-site" or remote site bacterial culturing system overcomes the above problems experienced by prior art systems. Moreover this system permits waste water plant operators to determine precisely which microbes are to be cultured, the order of culturing, and the volume of bacteria to be produced. This mitigates the problems of time, transportation and expense (along with loss of activity) discussed above. This also permits waste water plant operators to produce precisely cultured bacterial media on an "as needed" basis. In this manner, costs can be reduced and ecological concerns can be more adequately addressed.

SUMMARY OF THE INVENTION

Briefly, in one aspect of the present invention is a waste water treatment system comprising a primary culturing means or basin such as a tank, in liquid communication with an acclimator basin. The primary culturing basin optionally includes air input means, water input means, a light source, a removable nutrient input means, a unique effluent collector (described below), and means to connect the primary culturing basin to the acclimator basin.

The acclimator basin includes a light source, an input means from the primary culturing basin, input means from the waste water stream to be treated, high surface area bacteria culturing media and output means to the waste water stream which is to be treated. The bacterial culturing system of this invention may also be used to culture non-plant species where such species are to be used to treat waste water effluent streams in accordance with the present invention. Thus, while the term "bacterial" culturing system is used herein, it should be understood that the present invention may be applicable to the growth and culturing of other species.

DETAILED DESCRIPTION OF THE INVENTION

Figure 1:
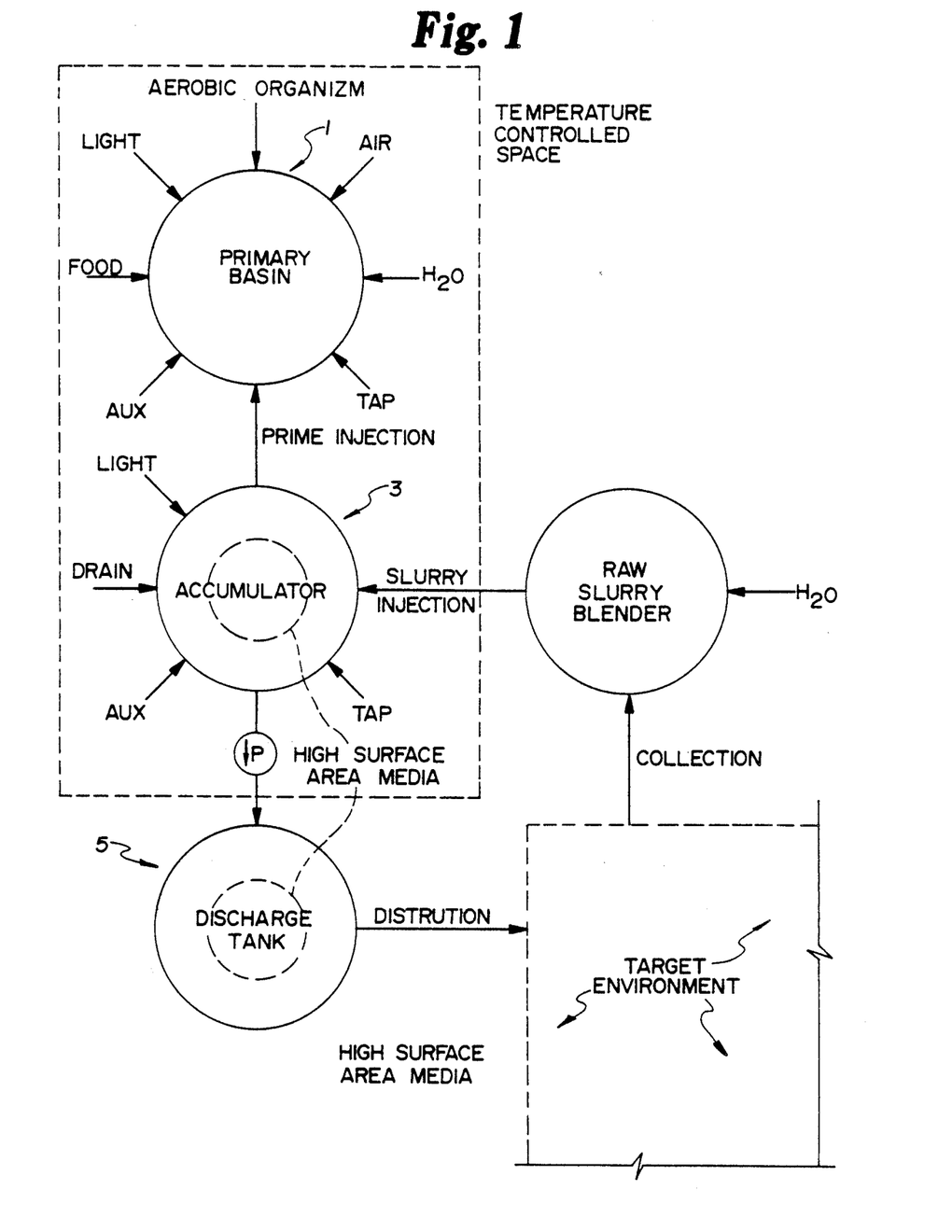
FIG. 1 is a schematic representation of a preferred bacterial culturing system of the present invention.

Referring now to the figures wherein like numerals are used to refer to like portions of the respective figures, FIG. 1 depicts a schematic representation of a preferred embodiment of the present invention. Contained within the temperature controlled space schematically defined by a dotted line is a primary basin 1 and acclimator basin 3. Primary basin 1 is a multiple zone bacteria culturing basin or tank and, as an example, could have a volume of 250 gallons.

As shown, primary basin 1 has air input means, a light source, a food source, and a water source. Per the arrow at the top of the box, culturing of aerobic bacteria is contemplated in the system of FIG. 1. Were anaerobic bacteria to be cultured, anaerobic organisms would be input. (It would be important to exclude sources of air from the system were anaerobic bacteria to be grown.)

Primary basin or culturing basin 1 also includes auxiliary drainage means as shown. Material cultured in the primary basin is poured or flows into the acclimation basin 3, also schematically depicted in the dotted line box of FIG. 1.

Acclimation basin 3 has a source of light and desirably contains a high surface area media discussed below. The acclimator basin is intended to provide an opportunity for bacteria produced in the primary basin a limited time period to be exposed to, and therefore, to be acclimated to plant liquid e.g., the material ultimately to be treated.

Acclimation is necessary when, for example, toxic waste is to be treated by the bacteria produced in the present system. A typical volume for an acclimator basin would be approximately 200 gallons. The time for acclimation of bacteria could be arranged from a very short time period to up to 60 hours. The present invention contemplates utilization of the acclimator or acclimation basin only when necessary, such as, for example, when toxic wastes are to be treated. In a particular system, several acclimation basins may be employed. The acclimation step itself is accomplished by mixing primary basin cultured media with approximately ten percent plant water.

Proceeding from the acclimation basin or tank 3, the now acclimated bacteria flows, or is pumped (e.g., by pneumatic pump depicted by a circle "P"), into a discharge tank or bay discharge tank 5. This is simply a holding tank providing storage for the acclimated bacterial medium for dispensing into the target environment shown in the lower right hand corner of FIG. 1.

The target environment is, of course, the material to be treated within the waste water treatment plant itself. As noted above, the target environment may contain water, a source of air, as well as the material to be treated such as, for example, sludge, FOG, toxic waste, or other materials. The acclimator basin, the discharge tank, and the target environment may all contain high surface area media discussed below.

Proceeding toward the top of FIG. 1 from the target environment, material is collected and sent to the raw slurry blender which is a simple water containment mechanism. The blender, as depicted, can be decanted or pumped into the acclimator basin 3 to provide the acclimation environment discussed above.

Figures 2, 3:
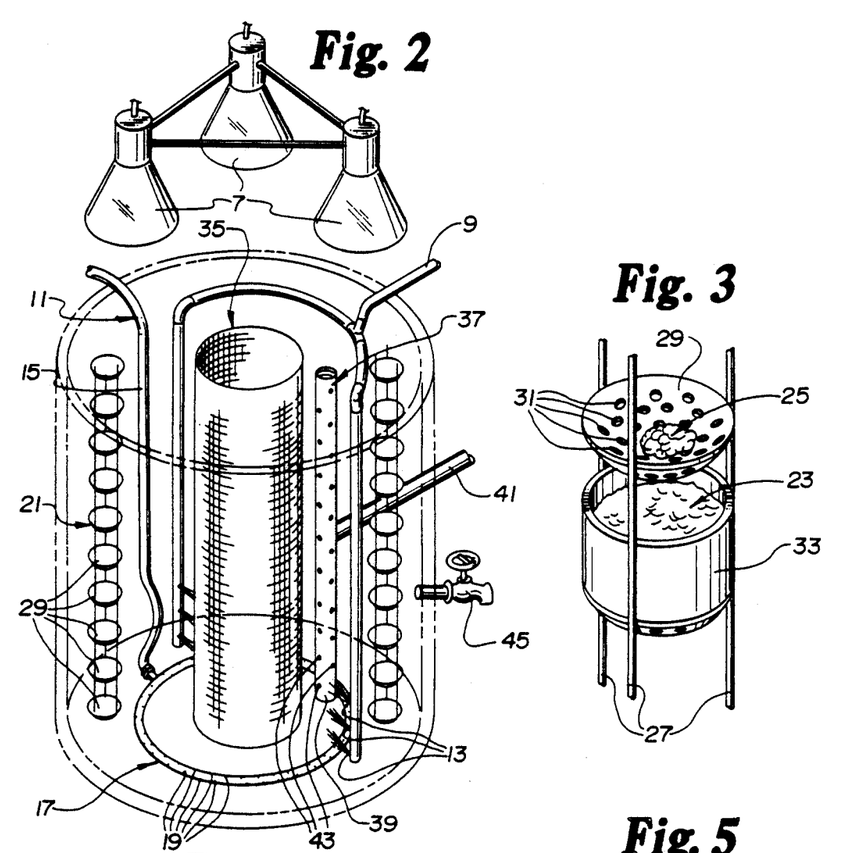
FIG. 2 is a perspective view of the primary basin or culturing basin schematically depicted in FIG. 1.
FIG. 3 is a detailed perspective depiction of the nutrient suspension means shown in FIG. 2.

FIG. 2 is a perspective view, with parts cut-away and shown in phantom, of primary basin 1. Starting from the top, the source of light is a series of sun lamps 7. One or more sun lamps, or other source of desired radiation e.g., to induce photosynthesis, may be selected. The preferred arrangement of sun lamps 7 would be disposed approximately one foot above the primary basin 1.

Inputting into the primary basin 1 are the water input means 9 and air input means 11. Water source 9 is, for example, a water injector comprising an input pipe 11 which leads to a series of outlet means which, in this instance are mixer nozzles 13. The mixer nozzles 13 are disposed near the bottom of the primary basin 1 and by virtue of their location help to mix materials contained in primary basin 1.

Air source 11 comprises, in this embodiment, a flexible input hose 15 leading to a circular aeration ring 17. The aeration ring 17 includes a series of air holes 19 which, when air is forced therefrom, permits mixing of materials in primary basin 1. In this embodiment, air source 11 can be located at several levels within primary basin 1 merely by moving the assembly up or down in basin 1. Thus, various degrees of aeration may be created at different zones within primary basin 1. In the instance where anaerobic bacteria are to be cultured, air source 11 would be excluded from this arrangement.

Primary basin 1 includes a nutrient input means or food holder 21. Food holder 21 can be used to input either liquid food sources 23 or solid food sources 25.

As is more completely shown in FIG. 3, nutrient input means 21, in this embodiment, includes a series of vertically disposed suspension means or support means such as rods 27. Rods 27 support solid food holders which, in this example are one or more plates 29 having perforations 31 formed therein. Plates 29 in this embodiment are disk-shaped. Preforations permit liquid material in primary basin 1 to circulate in and around solid food 25 contained on plates 29. Plates 29 may be of any desired shape which adequately supports unpackaged solid food, solid or liquid food encased in a dissolvable media envelope, or food packaged within a permeable membrane.

Nutrient input means 21 can be used to input liquid food 23. Where liquid food or nutrients are to be disposed within basin 1, a cup 33, rather than plates 29 may be employed. One or more of a series of plates 29 may be employed depending upon the user's preference.

Of particular note is the fact that the nutrient input means in the present invention is preferrably removable from primary basin 1. In this manner, nutrient input means 21 has a "drop-in" character which permits liquid and solid nutrient additives to be added at various times or stages in the culturing cycle. Nutrient input means 21 may also be used to dispose desired additives e.g., foods, vitamins, minerals, buffers, and dispersing agents, to assist in the culturing process, and limiting agents to retard growth of undesirable microorganisms.

Generally centrally disposed within primary basin 1 is a high surface area, substantially cylindrical prime basket 35. The substantially cylindrical prime basket 35 is removable from the primary basin 1. The basket 35 has an outer surface which comprises a permeable membrane made of a material such as nylon or other cloth, woven plastic, or metal screen. The membrane functions to hold a media which can vary in density. Typically, the media can vary from less dense material such as ceramics, charcoal brickettes, or plastic packing material, to more dense material such as silica sand, fine-ground anthracite, or garnet sand.

A positive or negative charge can be maintained on the media. This feature enables more efficient collection of bacteria. Bacteria can more optimally be adhered to the media while culturing by placing a positive charge on the media, if the bacteria are attracted to a positive charge, and by placing a negative charge on the media, if the bacteria are attracted to a negative charge.

The charging of the media can also function to facilitate "dumping" of the bacteria. If the bacteria are attracted to a negative charge, a positive charge can be given to the media when dumping is desired, and, if the bacteria are attracted to a positive charge, a negative charge can be given to the media when dumping is desired. The charging of the media with a charge opposite that to which the bacteria would be attracted, would be effected when discharging from a specific tank is desired to be accomplished.

Contained within primary basin 1 also is a unique vertically-disposed effluent collector 37. In this embodiment, effluent collector 37 comprises an upward standing vertical collection pipe 39 connected to a discharge pipe 41. Collection pipe 39 is vertically disposed and contains a generally vertical series of perforations or holes 43 therein. This unique collection means or withdrawal means, with its series of vertically disposed holes, collects a very homogeneous sampling of materials contained at the various levels within primary basin 1. In this manner, essentially without regard to the location of air source 11, a substantially homogeneous sampling of materials within primary basin 1 will be collected and discharged into acclimator basin 3. Primary basin 1 optionally includes auxiliary discharge means 45 e.g., a tap.

It should be noted that within primary basin 1 there may be several zones differing in their aerobic character. For example, since air input into primary basin 1 from the air source 11 tends to rise to the top, a substantially anaerobic zone may be created near the bottom of basin 1, a faculative zone in the intermediate portion of basin 1, and a substantially aerobic zone near the top of basin 1. Collector 37 would tend to mitigate these differences by withdrawing effluents from all levels within basin 1.

Figure 4:
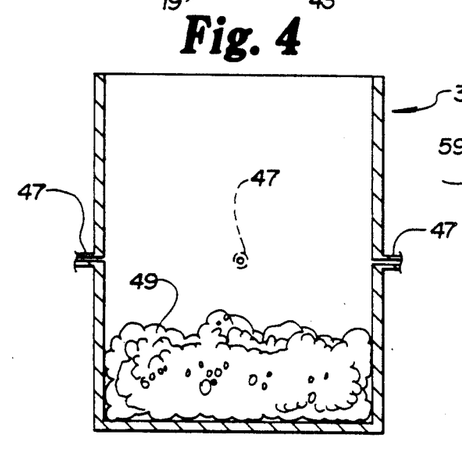
FIG. 4 is a cross-sectional view of the optional acclimator basin depicted in FIG. 1.

FIG. 4 is a cross-sectional representation of an acclimator basin 3 of the present invention. As noted above, an acclimator basin is necessary where bacteria cultured in basin 1 needs to be exposed (i.e. acclimated) to toxic materials contained within a waste water effluent stream to be treated.

Acclimator basin 3 includes liquid access means or ports 47 which may be used for inputting or outputting liquids. Acclimator basin 3 optionally may include a light source (not shown). In a typical configuration, acclimator basin 3 would be a 200 gallon tank.

Also contained within the acclimator or acclimation basin 3 would be high surface area bacteria culturing media 49. High surface bacteria culturing media 49 can include materials such as charcoal, sand, coal, or garnet. Each of these materials provide a high surface area which permits bacteria to multiply and be acclimated to waste water effluent streams. For example, one or more of a series of carbon panels $4'' \times 24'' \times 24''$ in dimension may be disposed within acclimator basin 3. As shown, high surface area material may be disposed in the bottom of basin 3. Acclimator basin 3 may also include an air source (not shown) and would normally include an input source for the waste water stream ultimately to be treated (also not shown).

Figure 5:
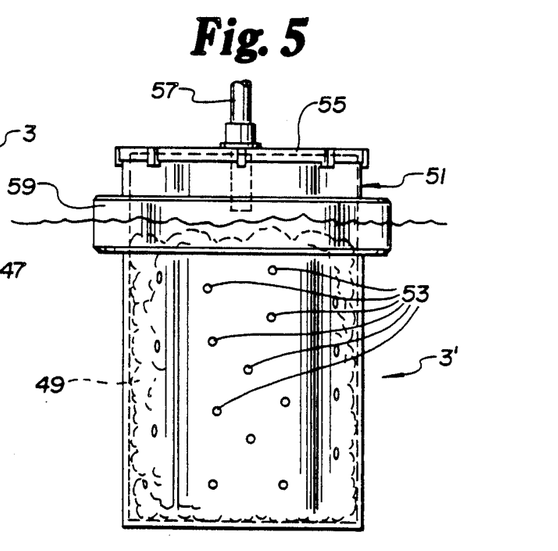
FIG. 5 is a cross-sectional view of an acclimator basin schematically depicted in FIG. 1 such as might be employed where the bacteria are to be acclimated.

FIG. 5 is an acclimator basin 3' that could be used to acclimate anaerobic bacteria. Acclimator basin 3' would normally be disposed below the liquid level of a larger tank. As such, acclimator basin 3' includes containment means 51 (e.g., a basket having a series a perforations 53).

Acclimator basin 3' includes a cover 55 and a distribution conduit 57. The entire assembly would be suspended in water (e.g., by a flotation ring or rings 59). Contained within acclimation basin 3' is the optional high surface area bacterial culturing media 49 discussed above.

Figure 6:
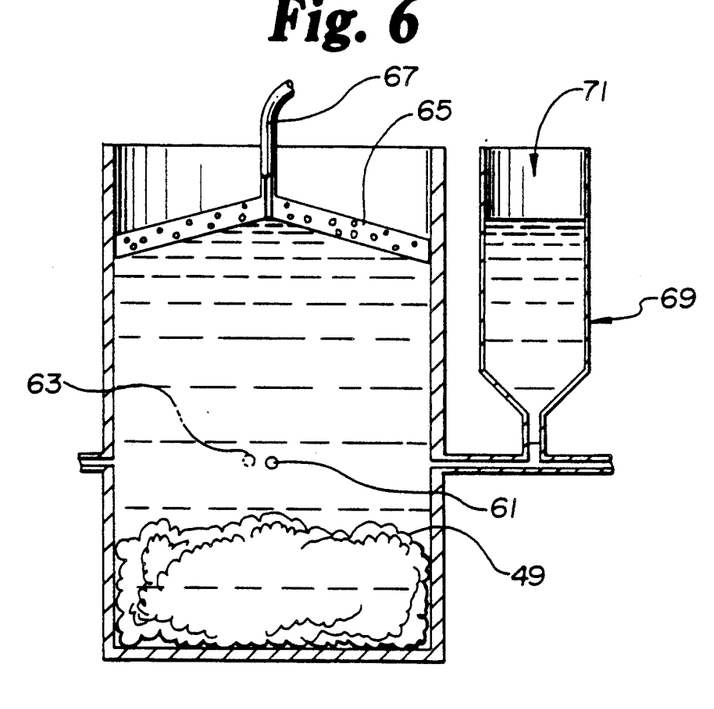
FIG. 6 is yet another depiction of an acclimator basin which includes optional auxiliary nutrient input means.

FIG. 6 depicts an alternative acclimator basin having an auxiliary input means. As shown, acclimator basin 3 contains high surface area media 49. It has a slurry injection port 61, an auxiliary output port 63, and a floating cap 65 which includes an optional asperator 67. As shown, acclimator tank 3 in FIG. 6 includes an auxiliary tank 69 which may be used to input various liquid media. For example, auxiliary tank 69 may be used to store a quantity of input food 71. Water or air can then be used to force materials contained within the auxiliary tank 69 into acclimator basin 3. Waste water effluent streams from the plant also could be used to mix with materials contained in auxiliary tank 69. In this embodiment, injector 71 is used to dispense materials within the auxiliary tank into basin 3.

Description of a Typical System

Figure 7:
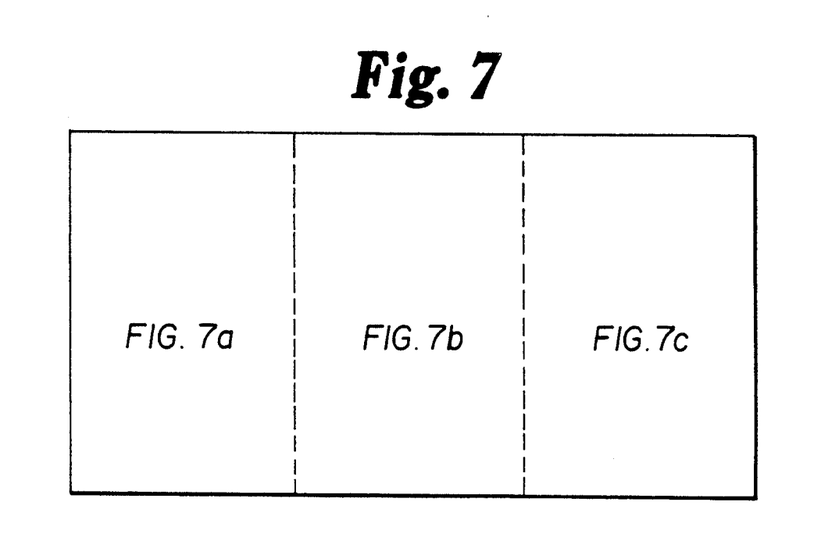
FIG. 7 is a schematic layout of a culturing basin/acclimation basin system of the invention.
Figure 7A:
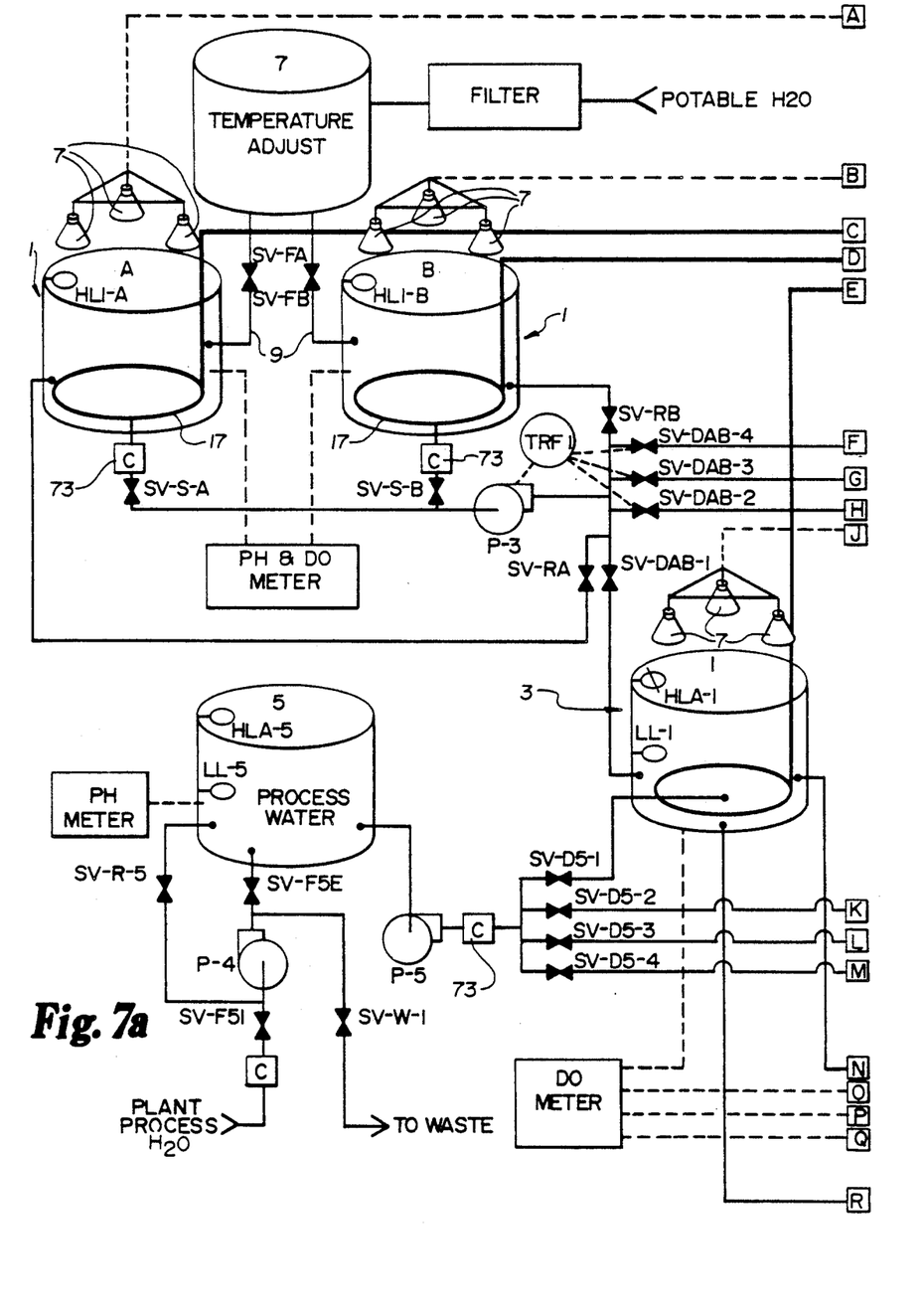
FIGS. 7a, 7b and 7c show the details of the basin/acclimation basin system of the invention; the relationship between sections a, b and c being shown in FIG. 7.
Figure 7B:
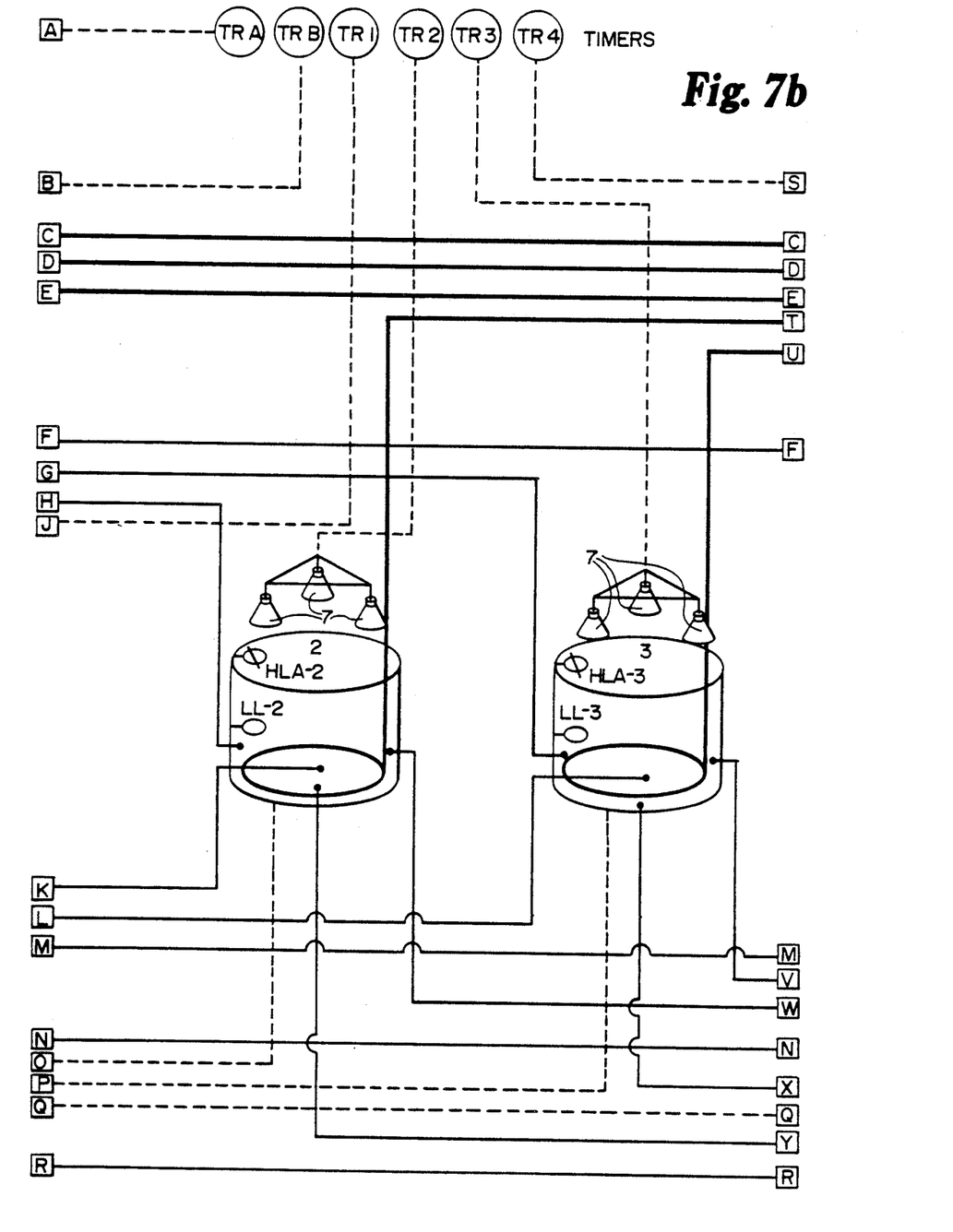
Figure 7C:
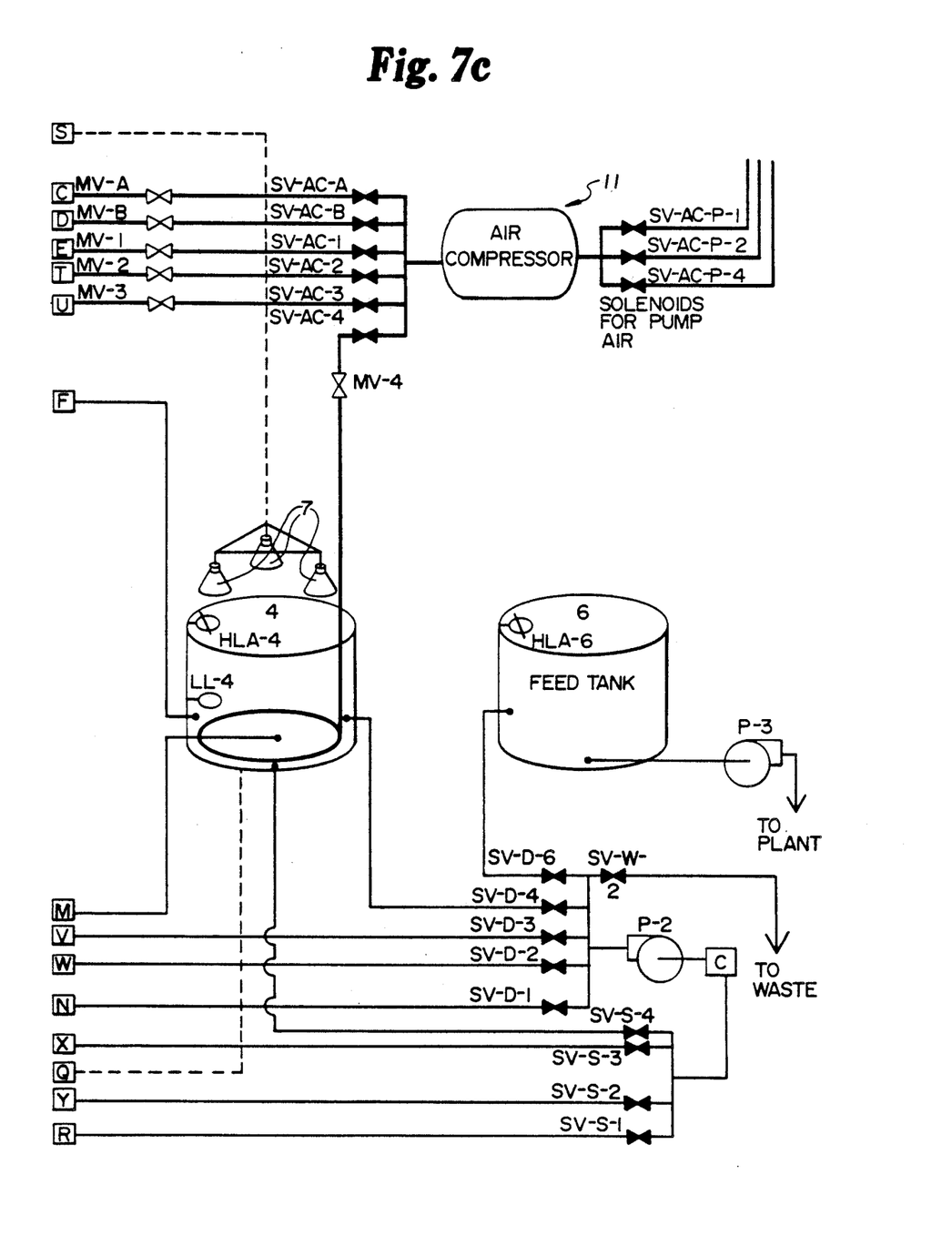

As is generally known, culturing of bacteria must be done in non-chlorinated water. Also, culturing must be accomplished at various specific temperatures depending upon the particular bacteria to be cultured. Thus, in a typical operation, it may be necessary to pass water obtained from a local utility through a dechlorination means e.g., a dechlorination filter. Further, it may be necessary to adjust the water input means temperature, e.g., by heating it or cooling it. Lastly, it may be necessary to adjust the acidity or basidity of culturing input streams. All of these steps may be accomplished in an optional preculturing tank which would be contructed and would be connected to the primary culturing basin or first bacterial culturing basin of the invention. Thus, as shown in FIG. 7, tank denominated 7 and having the title "temperature adjust" comprises a water input means or water source 9 of the invention.

Sun lamps 7 or primary culturing tanks A and B and acclimation basins 1–4 also are shown. A series of timers TRA, TRB, and TRY-4 control the times that the light sources are lit. Culturing basin timers generally run approximately 24 to 72 hours, whereas acclimation timers generally run for a time period of 1 to 24 hours.

Primary culturing tanks, designated A and B, and acclimation tanks 1–4 are connected by means of a series of solenoid valves ("SV") to an air compressor, thus providing the air input means or air source of the invention. Primary culturing tanks A and B are connected by two solenoid valves ("SV-S-A" and "SV-S-B") by means of a pneumatic metering piston pump ("P-1") to acclimation basins 1–4. Check valves 73 prevent liquid from flowing in the wrong direction, i.e., from the acclimation tanks into the culturing tanks.

By means of pneumatic pump P-1 and solenoid valves designated SV-DA D-4321, liquid from culturing tanks A and B may be pumped into any of acclimation basins 1, 2, 3 or 4. Moreover by means of pneumatic piston pump P-4, P-5, and solenoid valves D 5-1, 2, 3 and 4, input water streams from the plant also may be pumped into acclimation basins 1, 2, 3 or 4. As shown, and in a preferred embodiment, circulation pump P-2 and the series of solenoid valves connected thereto may be used to circulate materials between acclimation basins 1, 2, 3 or 4. Lastly, circulation pump 2 is used to pump material from acclimation basins 1, 2, 3 or 4 into feed tank 6 and via pump P-3 to the plant.

In a typical operation, culturing liquid in tanks A and B is replenished at the same time water is pumped therein. Culturing lights are then turned on for a period of time determined by the variety of bacteria to be cultered. As the lights are turned on, the diffusers (e.g., via the air compressor) are also turned on. Note that materials in primary culturing tanks A and B optionally may be circulated between each other.

After the requisite culturing time period, tanks A or B are pumped or decanted into the acclimation basins. Generally, the materials from tanks A and B are decanted into the acclimation basin(s) at the lowest level. Solenoid valves depicted in FIG. 7 are used to distribute materials from culturing tanks A and B. Pump P-1 is used to distribute the materials from culturing tanks A and B.

FIG. 7 indicates a "process water" tank having a number designation of 5. Process water tank 5 is a preferred input means from the waste water stream to be treated as described above. Process water tank 5 (via pump P-4) brings liquid from the effluent waste water stream or plant into which acclimator bacteria ultimately are dispersed. The process water tank generally has high level and low level indicators which, in turn, shut off or actuate pump P-4 to either bring water in from the plant or stop such water input.

In operation, the process water tank is filled to the appropriate level. The pH of the materials in the tank is adjusted, and other additives or buffers are mixed into the process water. The process water tank and acclimator tanks are electrically interconnected so that the low level of the process water tank provides enough material to the acclimation tanks to permit any on-going acclimation process to be completed. Thereafter, no further acclimation cycles will be started until after the process water tank is completely filled.

Pump P-5 transports process water into acclimation tanks 1–4. Downstream from pump P-5 is a check valve 73 which prevents process water flowing in the wrong direction (that is, from the acclimation tanks to the process water tank).

Steps in Bacterial Acclimation

Acclimation tanks 1–4 contain high level and low level detectors. In operation, tanks 1–4 are filled with liquid until high level alarms are tripped, at which time the filling process is discontinued. As cultured bacteria from tanks A and B are pumped into tanks 1–4, water from the process water tank can simultaneously be pumped into acclimation tanks 1–4.

Process water is pumped into the acclimation tanks by means of a metered pump which determines the ratio of process water to cultured bacteria, according to the bacteria to be acclimated. At the completion of the acclimation tank filling process, culturing tanks A or B will be emptied through approximately 25 percent of their original volume and will be ready to restart the culturing process.

Upon filling of acclimation basins 1–4, timers controlling light source means are energized to provide light to the acclimation basins. Second, third or fourth acclimation cycles are contemplated to the extent that cultured media from culturing tanks A and B are available without depletion of the materials contained therein below their low level. Obviously, to the extent automation is comtemplated, any of the above steps may be electronically controlled (e.g., by computer).

As within the contemplation of the present invention the auxiliary acclimation means would be included. Such auxiliary of acclimation means would be used when, for example, additional acclimation time is necessary for the cultured bacteria to withstand the adverse environment into which it will be ultimately dispersed.

In the situation where additional acclimation is required in auxiliary acclimation tanks, a metered portion of the process water in tank 5 also must be metered into the auxiliary acclimation tanks. Where there is a concern for dissolved oxygen ("DO"), it may be necessary to place dissolved oxygen meters in the particular tank in which dissolved oxygen is important. The amount of oxygen dissolved in a particular effluent would then be adjusted (e.g., by controlling the air compressor and valving mechanisms to the compressor to the tank in question).

Feed Tank

Feed tank (number 6 in FIG. 7) is generally at least twice as large as any of the existing tanks from which it receives processed material. Feed tank 6 is part of the output means to the waste water stream to be treated as discussed above. Generally it will include a high level alarm which prevents overflow. Feed tank 6 pumps material to plant effluent streams via pump P-3 as shown.

Numerous characteristics and advantages of the invention have been set forth in the foregoing description. It will be understood, of course, that this disclosure is, in many respects, only illustrative. Changes can be made in details, particularly in matters of shape, size, and arrangement of parts without exceeding the scope of the invention. The invention's scope is defined in the language in which the appended claims are expressed.

What is claimed is:

1. A bacteria culturing system for waste water treatment, comprising:
   (a) a primary culturing basin including:
      (i) a light source;
      (ii) water input means;
      (iii) removable nutrient input means vertically disposed therein;
      (iv) an effluent collector comprising a vertical collection pipe having vertically disposed holes therein; and
      (v) effluent collector discharge means connected to said effluent collector which is in fluid communication therewith; and
   (b) an acclimator basin including:
      (i) a light source;
      (ii) input means from the primary culturing basin;
      (iii) input means from the waste water to be treated;
      (iv) high surface area bacteria culturing means; and
      (v) output means to the waste water to be treated.

2. A system according to claim 1 wherein the water input means includes pre-treatment means in which at least one of pH, temperature and other factors are adjusted.

3. A system according to claim 1 wherein the input means from the waste water stream to be treated is a separate process water treatment means.

4. A system according to claim 1 wherein the high surface area bacteria culturing means in the acclimator basin is selected from the group consisting of coal, sand, charcoal, garnet, ceramic media, or lava stone.

5. A system according to claim 1 wherein the removable nutrient input means comprises two or more vertically disposed rods supporting one or more horizontally disposed plates, said plates having perforations formed therein.

6. A system according to claim 1 wherein the removable nutrient input means comprises vertically disposed rods supporting liquid-containing cups from which liquid nutrients may be dispensed.

7. A system according to claim 1 wherein the primary culturing basin further comprises a centrally disposed cylindrical water permeable prime basket, said prime basket including high surface area bacteria culturing means.

8. A system according to claim 7 wherein the high surface area bacteria culturing means is selected from the group consisting of coal, sand, plastic media, garnet, or ceramic media.

9. A system according to claim 1 wherein the primary culturing basin further includes air input means.

10. A system according to claim 9 wherein the air input means includes an air compressor.

11. A bacteria culturing system for waste water treatment, comprising:
    (a) a primary culturing basin including:
       (i) a light source;
       (ii) water input means;
       (iii) nutrient input means disposed therein;
       (iv) an effluent collector; and
       (v) an effluent collector discharge means connected to said effluent collector which is in fluid communication therewith;
    (b) an acclimator basin including:
       (i) a light source;
       (ii) input means from the primary culturing basin;
       (iii) input means from the waste water to be treated;
       (iv) high surface area bacteria culturing means; and
       (v) output means to the waste water to be treated.

12. A system according to claim 11 wherein the water input means includes a pre-treatment means.

13. A system according to claim 12 wherein the pre-treatment means is a tank in which pH, temperature or other factors can be adjusted.

14. A system according to claim 11 wherein the input means from the waste water stream to be treated is a separate process water treatment means.

15. A system according to claim 11 wherein a high surface area bacteria culturing means in the acclimator basin is selected from the group consisting of coal, sand, charcoal, garnet, ceramic media, or lava stone.

16. A system according to claim 11 wherein the nutrient input means is removable.

17. A system according to claim 16 wherein in the removable input means comprises two or more vertically disposed rods supporting one or more horizontally disposed plates, said plates having perforations therein.

18. A system according to claim 11 wherein the primary culturing basin further comprises a centrally disposed cylindrical water permeable prime basket, said prime basket including high surface area bacteria culturing means.

19. A system according to claim 18 wherein the high surface area bacteria culturing means is selected from the group consisting of coal, sand, plastic media, garnet, or ceramic media.

20. A system according to claim 11 wherein the effluent collector comprises a vertical collection pipe having vertically disposed holes therein.

21. A system according to claim 11 wherein the air input means includes an air compressor.

* * * * *